United States Patent [19]

Ledoux et al.

[11] Patent Number: 5,576,466

[45] Date of Patent: Nov. 19, 1996

[54] PROCESS FOR THE ISOMERISATION OF STRAIGHT HYDROCARBONS CONTAINING AT LEAST 7 CARBON ATOMS USING CATALYSTS WITH A BASE OF MOLYBDENUM OXYCARBIDE

[75] Inventors: Marc J. Ledoux; Jean-Louis Guille, both of Strasbourg; Cuong P. Huu, Saverne, all of France; Edd Blekkan, Flataasen, Norway; Eric Peschiera, Avon, France

[73] Assignee: Pechiney Recherche, Courbevoie, France

[21] Appl. No.: 337,368

[22] Filed: Nov. 8, 1994

[30] Foreign Application Priority Data

Nov. 18, 1993 [FR] France ................... 93 14199

[51] Int. Cl.⁶ .................................................. C07C 5/13
[52] U.S. Cl. .......................... 585/735; 585/734; 585/750; 585/751; 502/177
[58] Field of Search .................. 585/734, 735, 585/750, 751; 502/177, 178

[56] References Cited

U.S. PATENT DOCUMENTS

| 4,271,041 | 6/1981 | Boudart et al. ................ 252/438 |
| 5,139,987 | 8/1992 | Ledoux et al. ................ 502/177 |
| 5,196,389 | 3/1993 | Dubots ......................... 502/178 |
| 5,217,930 | 6/1993 | Dubots ......................... 501/88 |
| 5,308,597 | 5/1994 | Ledoux et al. ................ 423/440 |

FOREIGN PATENT DOCUMENTS

| 2216092 | 3/1993 | Australia . |
| 474570 | 3/1992 | European Pat. Off. . |
| 534867 | 9/1992 | European Pat. Off. . |

OTHER PUBLICATIONS

Reactions of 2- and 3-Methylpentane, Methylcyclopentane, Cyclopentane, and Cyclohexane on Activated Mo$_2$C, Pham–Huu et al, Journal of Catalysis 143, pp. 249–261 (1993). (month unknown).

Primary Examiner—Shrive Beck
Assistant Examiner—Timothy H. Meeks
Attorney, Agent, or Firm—Dennison, Meserole, Pollack & Scheiner

[57] ABSTRACT

A process for isomerizing straight chain hydrocarbons having at least seven carbon atoms by forming a reaction mixture including at least one of the straight chain hydrocarbons and hydrogen and passing the reaction mixture over a catalyst including a molybdenum compound, at least the surface of which is formed of molybdenum carbide partially oxidized in the form of at least one oxycarbide.

17 Claims, 6 Drawing Sheets

—— S(acy)  —— S(cyc)  ---- S(craq)

○ Pt / beta-zeolite (15 bar)
● MoO3 (15 bar)
■ Mo2C (6 bar)

PROCESS FOR THE ISOMERISATION OF STRAIGHT HYDROCARBONS CONTAINING AT LEAST 7 CARBON ATOMS USING CATALYSTS WITH A BASE OF MOLYBDENUM OXYCARBIDE

TECHNICAL BACKGROUND OF THE INVENTION

The invention is concerned with catalysts for the isomerisation of straight hydrocarbons into branched hydrocarbons which therefore have a better octane rating.

These isomerisation reactions are of considerable importance industrially. In fact, internal combustion engines require fuels with a high octane rating. This high rating used to be obtained by adding tetraethyl lead to the petroleum. To reduce lead pollution, the tetraethyl lead is replaced by other products with a high octane rating, either by aromatics which are also harmful to the environment or by tertiary ethers. These products make up the composition of unleaded petrol.

By way of illustration, the octane rating of isooctane (2-dimethyl 3-methylpentane) is, by definition, 100, and that of n-heptane is 0. A naphtha $C_5$-$C_9$ petroleum cut has an octane rating of 70, which, after gas reforming, is about 91, and, after tetraethyl lead has been added, is 94. Pure toluene has a rating of 97.

Avoiding tetraethyl lead and aromatics in fuels has meant that a great interest has been taken in finding isomerisation processes which enable branched isomers to be obtained from straight aliphatic hydrocarbons, the octane rating of which branched isomers is higher than that of their straight counterparts.

An isomerisation reaction of this kind is well-known to the skilled person: it is carried out by passing the hydrocarbon to be isomerised and which is diluted in hydrogen over a suitable catalyst at a temperature close to 350° C. At the outlet from the reactor a mixture is collected of different isomers which are branched to varying degrees, of cracked products which therefore contain fewer carbon atoms than tile starting hydrocarbon, and of cyclic products. The efficiency of the reaction can be assessed by the percentage of molecules of the starting hydrocarbon which are transformed into branched hydrocarbons, cracked products of cyclic products being regarded as undesirable.

The catalysts usually used are of the bifunctional kind: a dehydrogenating-hydrogenating function provided by precious metals, platinum-rhenium or platinum-irridium, and an isomerising acid function provided by the support, usually gamma aluminium doped with chlorine. Other catalysts then appeared which were composed of platinum with a zeolite support. Finally, more recently, a new class of catalysts has been found which was based on totally different chemical types since they were catalysts with a base of heavy metal carbides. These catalysts and the processes for their preparation are described in the following patent applications:

EP-A- 0 396 475 (PECHINEY ELECTROMETALLURGIE): Obtaining heavy metal carbides with a high specific surface area.

This application describes a process for obtaining heavy metal carbides with a high specific surface area, characterised in that a gaseous compound of said metal is reacted with a reactive carbon with a specific surface area of at least 200 $m^2/g$ at a temperature of between 900° C. and 1400° C., and the carbides thus obtained.

The examples in this application compare the activity of this new type of catalyst, particularly the catalyst with a base of tungsten and molybdenum carbides, with a conventional catalyst, $Al_2O_3$+0.25% platinum, for the isomerisation of methylcyclopentane and of n-hexane.

EP-A- 0 440 569 (PECHINEY ELECTROMETALLURGIE): Process for obtaining porous solid bodies with a base of refractory carbide by means of organic compounds and metal or metalloid compounds.

This application describes a process for obtaining porous solid bodies of a shape and porosity to suit requirements, of a carbide with a high specific surface area, characterised in that a carbonisable compound which is exclusively organic, polymeric and/or copolymerisable and capable of giving a carbonaceous solid skeleton is mixed with a metal or metalloid powder or one of its compounds which is reducible by carbon, the mixture is shaped, the organic compound is cross-liked or hardened, and is subjected to a heat treatment for the organic compound to be carbonised at between 500° and 1000° C., and then for carburation to be carried out.

EP-A- 0 474 570 (GIE PECHINEY RECHERCHE): A process for activation from the surface of carbides of heavy metals with a high specific surface area for the purpose of catalytic reactions.

This application describes a process for activation of carbides of heavy metals with a high specific surface area in order for them to be used as catalysts in chemical or petrochemical reactions, consisting in subjecting the carbides to an oxidation treatment which is carried out in a current of oxidising gas at a temperature of between 250° and 450° C. by keeping a temperature stage of at least 3 hours, then by cooling to ambient temperature, still in the presence of an oxidising current. Example 1 shows the comparison between a catalyst with a base of molybdenum carbide which is activated in accordance with the process described and a conventional catalyst with a Pt base for isomerisation of the n-hexane.

EP-A- 0 511 919 (coating) PECHINEY ELECTROMETALLURGIE): Catalytic system, in particular for post-combustion of the exhaust gases and the process for their production.

This application describes a catalytic system which is made up of a support on which the catalytically active product is deposited. The support has worthwhile mechanical or physical properties for the required operating conditions, but a mediocre specific surface area. The catalytically active product, a metallic carbide, is obtained by coating the support in a suspension of a reducible compound of the metal in a solution of an organic compound, carbonisation of that compound, reduction of the metallic compound, and carburation of the metal. The carbide thus obtained has a high specific surface area.

Preferably, the support is constituted by silicon carbide prepared by carbonisation of a paste containing silicon, carbon and an organic resin. In the examples, the catalytically active carbide is a molybdenum, iron, tungsten, or vanadium carbide.

EP-A- 0 534 867 (GIE PECHINEY RECHERCHE): Preparation of the catalyst from metallic oxides by reduction and partial carburation by reaction gases.

This application describes a catalyst for chemical and petrochemical reactions which is made up of an oxide of one of the transition metals, rare earth metals or actinide, e.g. molybdenum, comprising carbides and oxycarbides at the surface.

The manufacturing process consists in passing over the oxide the gaseous reaction mixture containing carbonaceous products which are to undergo catalytic chemical transformation at the temperature of that reaction. The carbonaceous products present in the mixture cause gradual carburation of the surface of the oxide and also a gradual increase in the efficiency of the catalyst.

The process is used, in particular, for the isomerisation of hydrocarbons for which molybdenum oxide $MoO_3$ is a preferred catalyst. The examples describe the isomerisation of n-hexane diluted in hydrogen.

To fully appreciate the problem with which the applicants were faced, a number of characteristic parameters of the isomerisation reaction should be defined. These parameters are as follows:

Conversion rate C (in %): ratio of the number of molecules of hydrocarbon transformed either by isomerisation or by cracking to the number of molecules passed over the catalyst.

Total selectivity S tot. (in %): ratio of the number of hydrocarbon molecules isomerised to the total number of molecules transformed either by isomerisation or by cracking.

Selectivity of acyclic products S acy. (in %.): ratio of the number of hydrocarbon molecules isomerised into acyclic products to the total number of molecules transformed either by isomerisation or by cracking.

Conventional, prior art catalysts with platinum permitted higher conversion rates and higher selectivities when the molecule to be isomerised contained 6 carbon atoms (n-hexane). However, when the hydrocarbons contained more than 6 carbon atoms, beginning with n-heptane, selectivity decreased considerably, whilst the conversion rate increased ("Isomerisation of C4–C7 paraffins on zeolithic catalysts"— M. Belloum et al., Revue de l'Institut Français du Pétrole—1991 vol. 41 p. 89–107).

This phenomenon is also illustrated in FIG. 6 where the conversion rate in a stationary state is shown along the x-axis and where the corresponding selectivity of isomerised products is shown along the y-axis.

FIG. 6 requires some explanation: firstly, the conversion rates and selectivities indicated are those observed after a few hours' operation when the catalyst has reached its stationary state and the values have stabilised. Also, the conversion rate depends on the reaction conditions: mass of catalyst, gas flow, concentration of hydrocarbon in the hydrocarbon-hydrogen reaction mixture, temperature, pressure; the same is true with respect to the selectivity.

However, a very negative correlation is to be seen between selectivity and conversion, and this correlation in simple terms means that the greater the number of molecules transformed (or the more the conversion rate increases) the greater the reduction in the percentage of desirable branched products. This reduction is clearly a serious hindrance to the use of hydrocarbons above $C_6$ as the source of branched hydrocarbons. Also, with such molecules which have a higher carbon content, cracking brings about the formation of free carbon which clogs the active surface of the catalysts and gradually makes them inefficient.

At the moment, hydrocarbons from $C_{7-C8}$ cuts are transformed by catalytic gas reforming to form aromatics used as additives in petroleum to increase the octane rating. However, new legislation has imposed a dramatic reduction in the proportions of aromatics in petroleum, as explained hereinabove.

Thus, despite the fact that in the past one solution was to add aromatics, it is now no longer possible, and a satisfactory process has to be found for obtaining isomerised products from long chain hydrocarbons. A process of this kind does not exist with current catalytic processes which either have insufficient selectivity of branched isomers or a conversion yield (product of conversion rate by selectivity) which is also inadequate to make an economical industrial process of it.

It is therefore worthwhile to find other types of catalysts which are capable of isomerising hydrocarbons of $>C_6$ cuts with high conversion rates and high selectivities of mono or multi-branched aliphatic isomers and with a minimum of aromatics and cracking carbon.

SUMMARY OF THE INVENTION

The inventors have found that catalysts with a base of molybdenum carbides and oxycarbides prepared according to one of the methods described hereinabove for isomerisation of the saturated carbides containing at least 7 carbon atoms.

OBJECT OF THE INVENTION

The invention therefore relates to a process for the isomerisation of straight hydrocarbons which have at least 7 (that is to say more than 6) carbon atoms by using catalysts with a base of molybdenum carbide and oxycarbide.

DETAILED DESCRIPTION OF THE INVENTION

Figure 1:
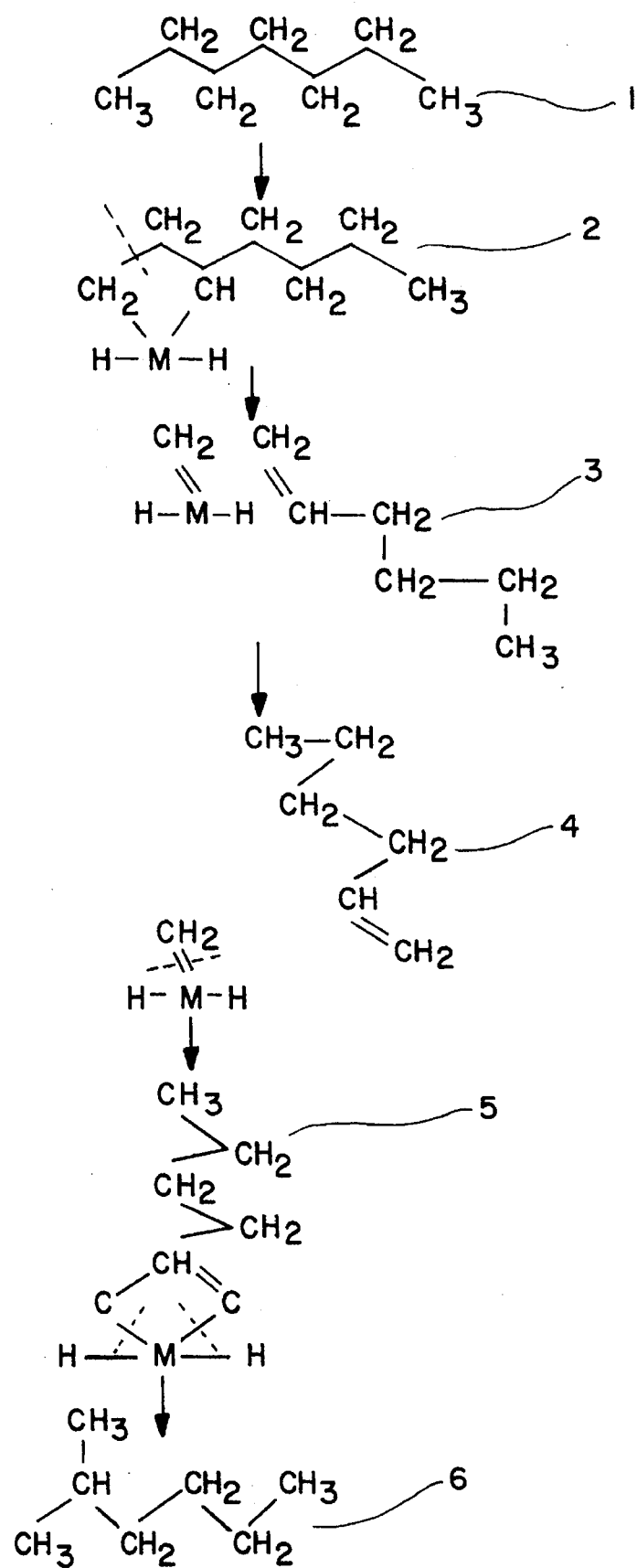
FIG. 1 shows the action of a catalyst with a molybdenum oxycarbide base which results in n-heptane with 2-methyl hexane.

The process which is the object of the invention is characterised by the combination of one specific catalyst and a reaction mixture under particular operating conditions.

The catalyst used comprises molybdenum compounds whose active surface, at least, which is in contact with the gaseous mixture to be treated is made up of molybdenum carbide which is partially oxidised in the form of one or more oxycarbides. This surface phase of oxycarbide has been proven by various physicochemical techniques such as X ray diffraction, programmed temperature reduction, X ray induced photoelectron spectroscopy, electronic scanning microscopy, electronic transmission microscopy and analysis by dispersion of X ray energy.

Several ways are possible of obtaining this surface oxycarbide.

a) From molybdenum carbide $Mo_2C$.

First of all it is possible to make molybdenum carbide with a large specific surface area:

either by reacting a volatile molybdenum compound $MoO_3$ on carbon with a large specific surface area, according to the teaching of Patent Application EP-A-0 396 475; it is not necessary to transform all the carbon into $Mo_2C$. It can be sufficient to have just a superficial layer of $Mo_2C$ and a core of I carbon, or, preferably, a core of a different carbide, e.g. SiC which acts as a support;

or by carbonizing a paste composed of a mixture of an organic resin, molybdenum powder or a reducible molybdenum compound, and by then heating the carbonised mixture to a temperature which is sufficient to reduce the molybdenum compound and carbonise the molybdenum obtained, according to the teaching of Patent Application EP-A- 0 440 569. As in the previous method, it is possible to obtain an active layer of molybdenum carbide on a support by immersing the support e.g. of silicon carbide, in a suspension of Mo or a Mo compound reducible in a carbonisable organic liquid. The suspension which impregnates the support is then carbonized, the Mo compound is reduced, and the molybdenum obtained is carbonised by heating, in accordance with the teaching of patent application EP-A-0 511 919.

This molybdenum carbide which is prepared using either method then has to be activated so that the oxycarbides which are responsible for the catalytic activity develop at the surface. This activation takes place, according to the teaching of patent application EP-A- 0 474 570, by subjecting the carbide to an oxidation treatment with a current of oxidising gas at a temperature of between 250° and 450° C.

This activation treatment must be followed by a balancing treatment consisting in passing over the activated catalyst at a temperature of between 250° and 450° C., preferably at a temperature close to 350° C., either a mixture of n-hexane and hydrogen, or the reaction mixture itself which is composed of a mixture of hydrogen and hydrocarbon with more than 6 carbon atoms.

b) From metal molybdenum or molybdenum oxide $MoO_3$.

It is also possible to start with metal molybdenum or molybdenum oxide $MoO_3$. If metallic Mo is used to begin with, the first step consists in oxidising the surface of the powder or the molybdenum grains into oxide $MoO_3$. Starting with either metallic Mo covered with a layer of $MoO_3$ or with pure $MoO_3$ it is possible, according to the teaching of patent application EP-A- 0 554 867, to develop an oxycarbide phase at the surface of the $MoO_3$. To that end, it is sufficient to pass a mixture of n-hexane and hydrogen or the reaction mixture itself which in composed of a mixture of hydrogen and hydrocarbon with more than 6 carbon atoms at a temperature of from 250° to 450° C. over the superficial $MoO_3$. Of course, the activation treatment using an oxidising gas is useless since an oxide is used initially, and not a carbide.

In addition to the catalysts cited above, particular mention should be made of a catalyst composed (i) of a support of a product which slightly interacts with molybdenum oxide $MoO_3$ and (ii) of a surface or active layer of molybdenum oxide $MoO_3$. Supports which slightly interact with $MoO_3$ in this way are, in particular, $TiO_2$, $SiO_2$, $ZrO_2$, and most particularly silicon carbide SiC.

These catalysts are manufactured in the following way:

The porous support is impregnated with a quantity of aqueous solution of ammonium heptamolybdate such that the content measured of metal molybdenum is between 5 and 16% of the weight of the support. The solution is poured, drop by drop, over the support. After drying for 8 to 20 hours at 100°–150° C., the catalyst is calcined in air at a temperature of between about 400° and 600° C. to calcine the molybdate and to obtain $MoO_3$.

The reaction mixture to which these catalysts are added, which are obtained by one of the methods described above, is a basic feature of the invention. In fact, whereas with catalysts with a base of precious metals, isomerisation of hydrocarbons with more than 6 carbon atoms, and, in particular, of n-heptane, is characterised by a considerable decrease in selectivity when the conversion rate increases, and is characterised by the depositing of carbon originating from cracking with catalysts with a molybdenum oxide base, it results in a high proportion of branched aliphatic hydrocarbons and a small proportion of cyclic and carbon compounds, this high selectivity being virtually constant, irrespective of tile conversion rate.

The reaction mixture of the invention comprises one or more straight hydrocarbons, with at least 7 carbon atoms, diluted in hydrogen. It can also contain straight hydrocarbons wit, less than 7 carbon atoms.

The preferred operating conditions of the isomerisation reaction are as follows:

temperature between 250° and 450° C.

concentration, by volume, of tile hydrocarbon(s) in the hydrogen of between 1 and 70% total pressure of the reaction mixture from 100 to 2000 kPa.

This superiority of catalysts with a Mo oxycarbide base over Pt-aluminium or Pt-zeolithic catalysts is explained by a different catalytic action.

As explained hereinabove, the catalysts usually used are bifunctional: a dehydrogenating-hydrogenating function is provided by precious metals: platinum-rhenium or platinum-iridium, and an isomerising acid function is provided by the support which is usually of gamma aluminium doped with chlorine or acid zeolites. Thus, it is not only the precious metal which takes a part in the catalytic activity, but also the aluminium or zeolithic support. The reaction can be explained as follows: firstly, dehydrogenation takes place of the hydrocarbon molecule which has been catalysed by the platinum; secondly, the dehydrogenated molecule is isomerised, the reaction having been catalysed by the acid function of the aluminium or zeolite, and thirdly the isomer obtained is rehydrogenated with the formation of an isomer of the starting product.

In the case of catalysts with a base of molybdenum oxycarbide, the proposed action is quite different. It has been described for $C_6$ cuts in the article, "Reactions of 2- and 3-methylpentane, methylcyclopentane, cyclopentane, and cyclohexane on actived $Mo_2C$" by Cuong Pham-Huu, Marc-J. Ledoux and Jean Guille, published in "Journal off Catalysis, 143, 249–261". It is illustrated for $C_7$ cuts in FIGS. 1 and 2.

Figure 2:
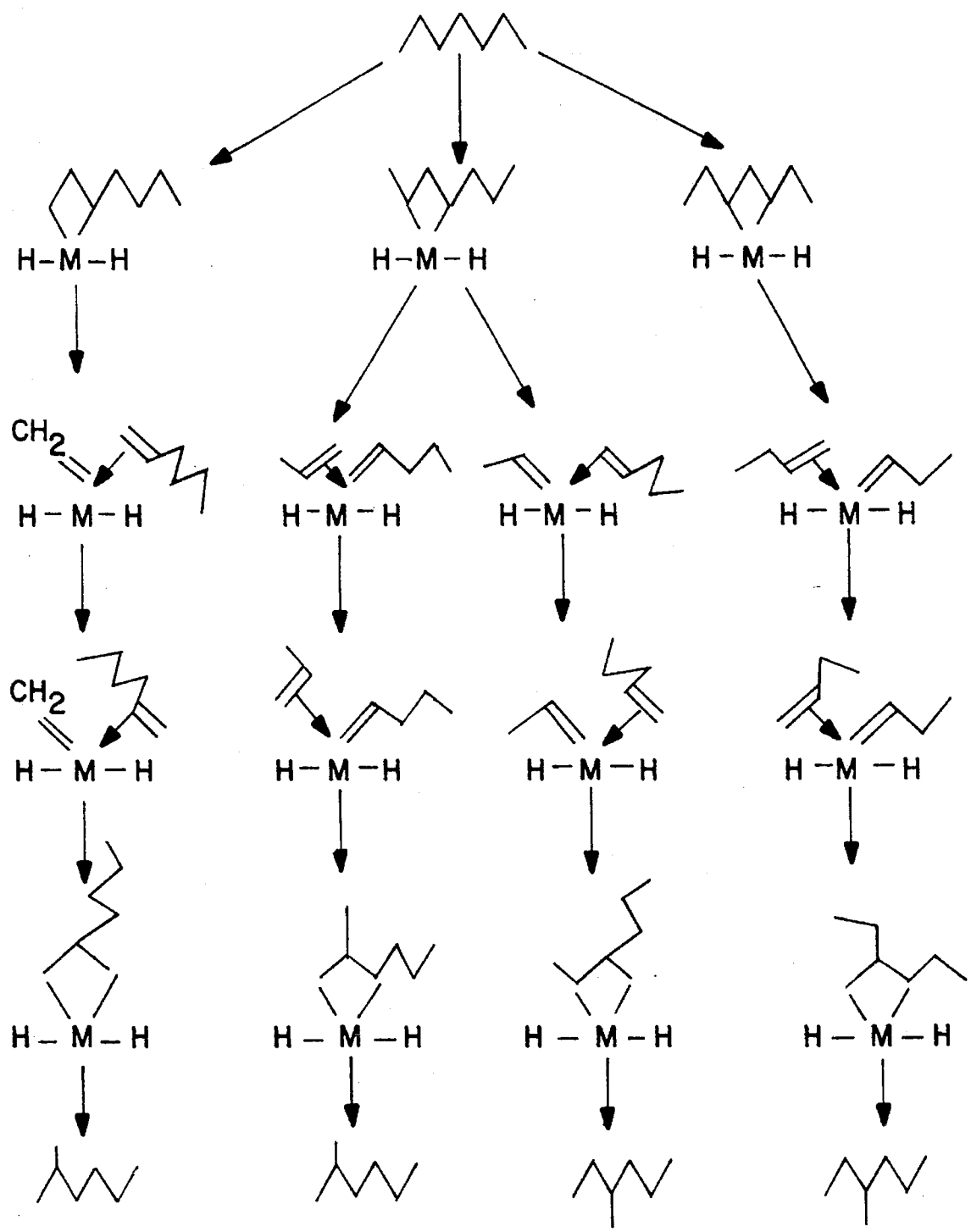
FIG. 2 also shows similar actions which result in two branched hexane isomers, 2-methyl-hexane and 3-methyl-hexane.

FIG. 1 which is more detailed shows the steps leading from n-heptane to 2-methylhexane. FIG. 2 also shows other possibilities based on a similar action and resulting in two branched hexane isomers, 2-methylhexane and 3-methylhexane.

The first step (FIG. 1) consists, always, starting with normal heptane (1), in the formation of a metallocyclic compound (2) composed of three carbon atoms and one molybdenum atom. The 3 carbon atoms can be carbons 1, 2, 3 (FIGS. 1 and 2A) or carbons 2, 3, 4 (FIG. 2B), or carbons 3, 4, 5 (FIG. 2C).

In the second step, FIG. 1, the bond between carbons 1 and 2 is broken, and the two compounds (3) are obtained: a metallic compound provided with a methylidene radical and 1-2 hexene.

Returning of the hexene molecule leads to a third step in the configuration (4).

In a fourth step, the opening of the double bonds results, once again, in a metallocyclic (5) isomer compound of the compound (2).

Finally, during the fifth step, the metallocyclic compound is decomposed, giving 2-methylhexane.

FIGS. 2B and 2C illustrate similar actions which compete with that described above.

It should be noted that the process for the isomerisation of straight hydrocarbons containing at least 7 carbon atoms according to the invention appears to be a worthwhile and very important application of catalysts with a base of molybdenum carbide and oxycarbide.

In fact, said process of the invention makes it possible to obtain very high isomerisation yields of acyclic products; this high yield is due to the fact that the process can be carried out in such a way that there is a high conversion rate (easily exceeding 50%, up to thermodynamic equilibrium, that is to say from 80 to 95% according to the molecules obtained), without the selectivity being significantly affected which remains at a very high level. In other words, the selectivity is independent of the conversion rate, irrespective of the number of carbons of the hydrocarbon to be isomerized.

By way of comparison, isomerisation processes employing bifunctional catalysts (Pt or precious metals deposited on the aluminium or zeolithic support) do not permit such a result.

Thus, it should be noted that the action of bifunctional catalysis is not applicable to all hydrocarbons, particularly those with more than 6 carbon atoms, whereas the isomerisation action in the presence of oxycarbide works just as well for light hydrocarbons with a maximum of 6 carbon atoms as for long chain hydrocarbons with 7 and more carbon atoms.

Therefore, it will be possible to treat, on an industrial scale, not only heavier fractions of naphtha cuts (C8 to C10, for example) in order to transform them into acyclic isomers with a high octane rating, but also much heavier cuts, particularly those entering into the composition of fuels for diesel engines (C10 and above), or those giving oils and lubricants (C17 and above) for which isomerisation permits dewaxing and a reduction in viscosity (for oils).

EXAMPLES

The following examples will illustrate the process of the invention which is used with different hydrocarbons.

The results are given in table form to show, as a function of time t which has elapsed since the start of the reaction, that is to say since the start of the passage of the product to be isomerized over the catalyst, the value of a certain number of parameters which ape defined, as follows:

Conversion C (in %): patio of the number of molecules of n-heptane transformed either by isomerisation of by cracking, to the number of molecules passed over the catalyst.

Total selectivity S tot. (in %): ratio of the number of molecules of n-heptane isomerized, to the total number of molecules transformed either by isomerisation or by cracking.

Selectivity of acyclic products S acy. (in %): ratio of the number of molecules of n-heptane isomerised into acyclic products, to the total number of molecules transformed either by isomerisation or by cracking.

Selectivity of cracked products S crq. (in %): ratio of the number of molecules of n-heptane cracked, to the total number of molecules transformed either by isomerisation or by cracking.

The following equation exists: Stot+Scrq=100%

Examples 1 to 4 are concerned with the isomerisation of n-heptane according to the prior art in the presence of a bifunctional catalyst with a Pt and gamma aluminium base (example 1) or with a Pt and zeolithic base (example 2), according to the present invention, in the presence of a catalyst with a molybdenum oxycarbide base (example 3), and a comparison of the selectivity curves as a function of the conversion rates with a catalyst according to the invention and a Pt-zeolithic catalyst according to the prior art.

Example 5 is a comparison of these same curves for n-octane, whilst examples 6 and 7 are concerned with the isomerisation of hydrocarbons into C10 and C20, and example 8 is concerned with the isomerisation of n-heptane in the presence of a catalyst with a base of molybdenum oxycarbide which is deposited on a carbide support.

Example 1—Comparative, According to the Prior Art

Catalyst with a platinum base, with a gamma aluminium support

The chemical types resulting from the catalytic reaction concerned with n-heptane are as follows:

1) Isomerized products:

Acyclic products
 DMP=assembly of 2,2-dimethylpentane+2,3-dimethylpentane+2,4-dimethylpentane;
 M2H, M3H=2-methyl and 3-methyl hexane;
 E3P=3-ethylpentane;
 Multibr.=various multi-branched heptanes.

Cyclic products
 MeCyH=methylcyclohexane;
 EcyP=ethylcyclopentane;

Toluene.

Cyc=assembly of C5 cyclic compounds.

2) Cracked products:

C6+C1=1 mole hexane+1 mole methane;

C5+C2=1 mole pentane+1 mole ethane;

C4+C3=mole butane+1 mole propane;

2C3+C1=2 moles propane+1 mole methane;

3C2+C1=3 moles ethane+1 mole methane;

7C1=7 moles methane.

The catalyst is prepared from gamma aluminium having the following characteristics:

porous volume: 0.62 cm$^3$/g;

grain size of between 0.250 μm and 0.425 μm;

specific surface area: 217 m$^2$/g.

This aluminium is impregnated with a solution of H$_2$PtCl$_6$.xH$_2$O. After impregnation, the catalyst is dried in air at ambient temperature for 8 hours, then calcined at 400° C. for 2 hours. Reduction of the chloroplatinic acid takes place in a flow of hydrogen at 400° C. for 2 hours. A catalyst is thus obtained which comprises, by weight, 1.3% of platinum. The temperature is then lowered to 350° C., and the hydrogen is replaced with a mixture of n-heptane and hydrogen with a total pressure of 1013 hPa=1 atm, partial pressure of the n-heptane being 16.15 hPa.

In this example, the flow rate of the gaseous mixture is 40 cm$^3$/min, and the mass of the catalyst is 0.0245 g.

The conversion rates and selectivities are shown in Table 1 hereinafter.

TABLE 1

| Time (hours) | 0.25 | 2.5 | 8 | 10.5 | 15 | 25 |
|---|---|---|---|---|---|---|
| Conv. C (%) | 65 | 44 | 34 | 33 | 31 | 28 |
| Sel. tot (%) | 43 | 51 | 62 | 63 | 65 | 64 |
| Sel. acy (%) | 15 | 19.5 | 24.3 | 25 | 26 | 25 |
| Sel. craq (%) | 57 | 49 | 38 | 37 | 35 | 36 |

These results call for the following comments to be made:

The conversion rate of the catalyst decreases greatly during the first 8 hours of the reaction, passing from 65% to 34%, and it then decreases more slowly.

The selectivity of cracked molecules which is high at the start (57%) decreases and stays at a value close to 36%. As a corollary, the total selectivity of products increases from 43% to 64%. However, the isomers obtained are characterised by a high proportion of cyclic hydrocarbons, methylcyclohexane, ethylcyclopentane and toluene. This proportion of cyclic isomers increases mope quickly than the proportion of acyclic isomers, since, if the total selectivity increases by approximately 20 points, the selectivity of acyclic isomers only increases, for its part, by 10 points, so as to remain stationary at a low value of 25%.

Figure 3:
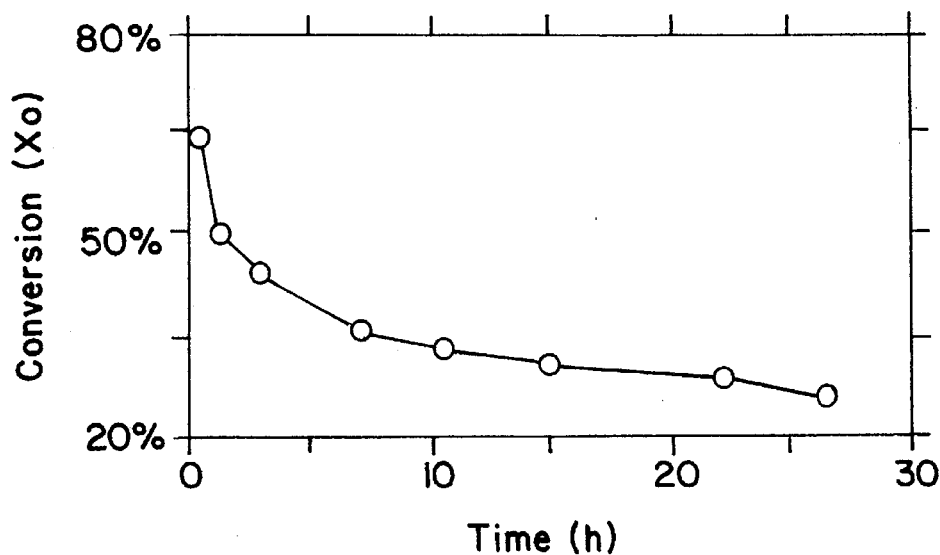
FIG. 3 shows, as a function of time, and for a prior art catalyst, platinum on aluminium, the conversion rate (percentage of heptane molecules having reacted, i.e. isomerised or cracked), FIG. 4 the selectivities of cracking products, cyclic products and acyclic products.
Figure 4:
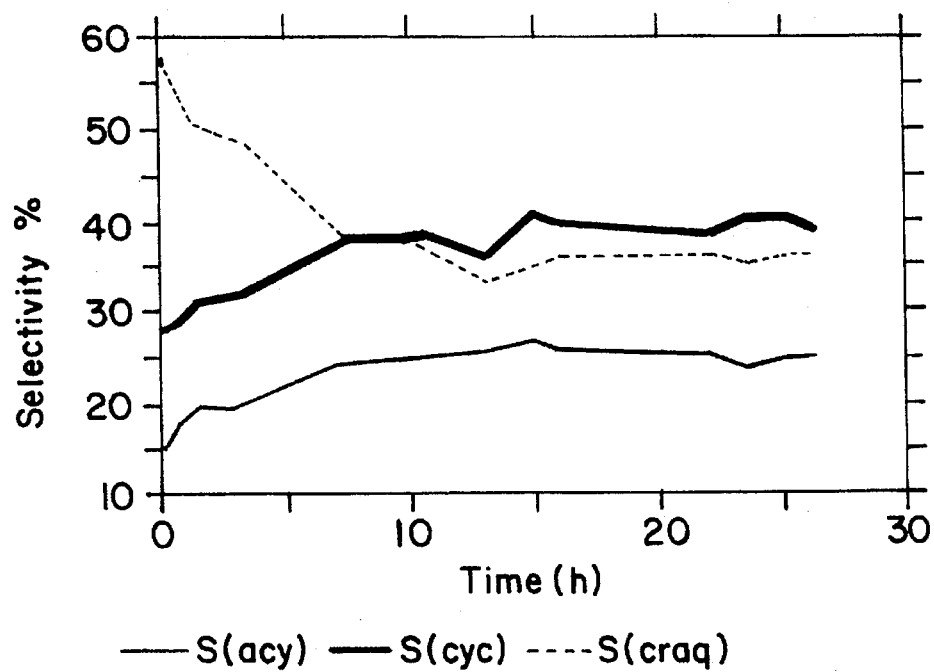

The results are illustrated in FIGS. 3 and 4.

FIG. 3 shows the development of the conversion rate as a function of time, and FIG. 4 shows the development, as a function of time, of the selectivities of cracking products, cyclic products and acyclic products.

Example 2

Isomerisation of n-heptane in the presence of a catalyst with a platinum base on a support of zeolite according to the prior art.

The catalyst comprises 0.8% Pt on a support of beta-zeolite.

Corresponding conversion for different of temperature and pressure values.

| Temperature K. | 523 | 523 | 523 | 548 | 573 |
|---|---|---|---|---|---|
| Pressure bar | 6.5 | 6.5 | 16.5 | 16.5 | 16.5 |
| Conversion % | 8 | 8 | 16 | 30 | 62 |
| Selectivity in C7 | 84 | 85 | 90 | 81 | 52 |

Figure 5:
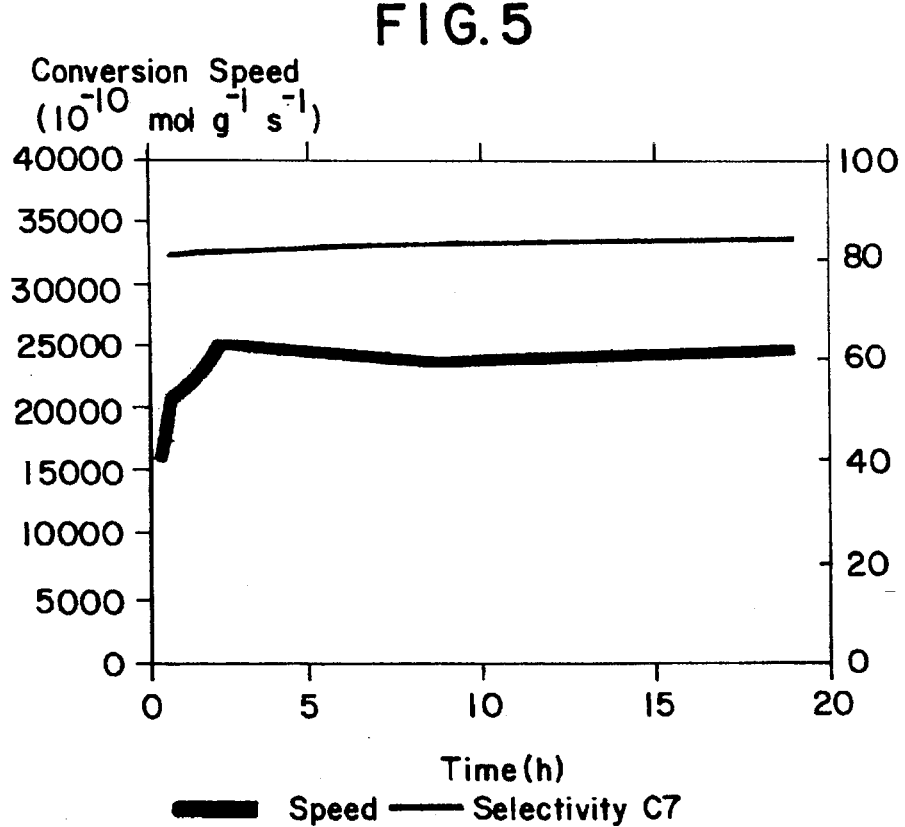
FIG. 5 also shows, as a function of time, and for a prior art catalyst with a base of platinum on zeolite, which promotes isomerisation, the conversion speed (percentage of molecules of n-heptane which have reacted per unit of time and weight of catalyst used, calculated on the basis of a reaction of the first order in relation to C7); this speed is proportional to the conversion rate and corresponds here to a low conversion rate of less than 20%.

Also, FIG. 5 gives, as a function of time, the isomerisation speed obtained from the conversion rate per unit of time and per unit of weight of the catalyst used, on the basis of a reaction of the first order in relation to C7. This speed is proportional to the conversion rate and corresponds, in the present example, to a low conversion rate which is always less than 20%.

Figure 6:
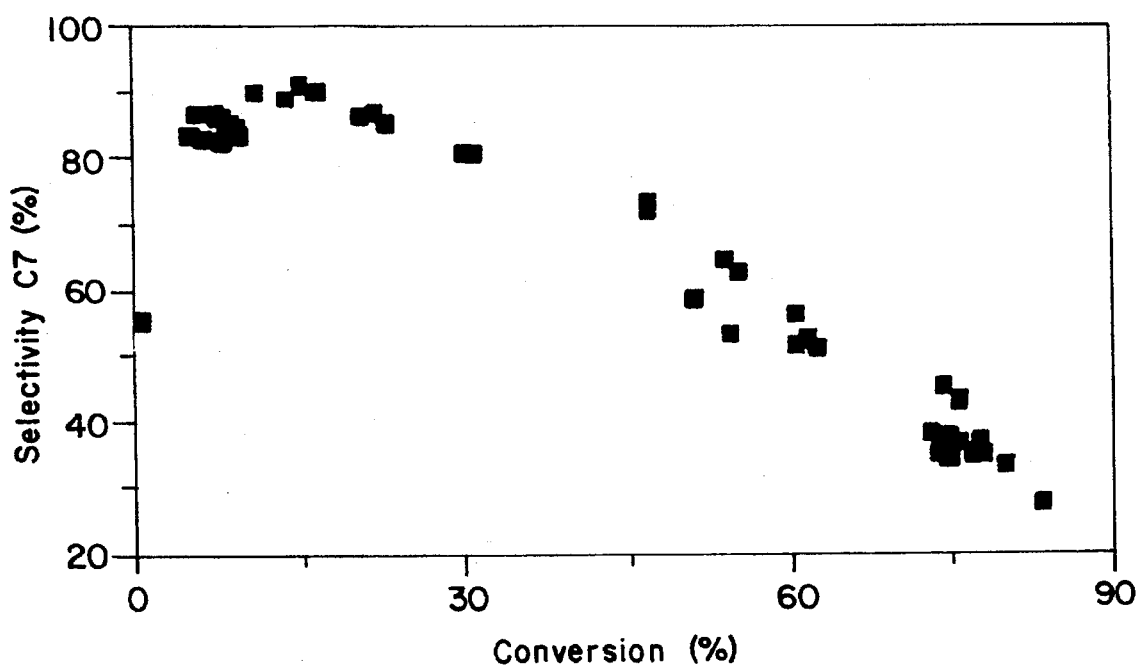
FIG. 6 shows the values of selectivities as a function of the conversion rates in a state of equilibrium, taken during a number of tests when the parameters of the isomerisation reaction: temperature, pressure, concentration of n-heptane in mixture, flow rate, for a prior art catalyst, Pt-zeolite, were varied.

As for FIG. 6, this gives the selectivity as a function of the conversion rate.

From this example it can be seen that it is never possible to have a high conversion rate and a high selectivity, thus a high conversion yield (which is the product of these two values) simultaneously.

A catalyst of this kind cannot therefore be used industrially to isomerize straight hydrocarbons with at least 7 carbon atoms.

Example 3

Isomerisation of n-heptane on molybdenum oxycarbide prepared from MoO$_3$. Influence of the total pressure of the system.

The same reactor is used as that described in Example 1, but the tests are carried out at three different total pressures:

3 bars=300 kPa test 5

6 bars=600 kPa test 6

20 bars=2000 kPa test 7

The other operating conditions are as follows:

| | Tests 5 and 6 | Test 7 |
|---|---|---|
| Temperature | 350° C. | 350° C. |
| Mass of MoO$_3$ | 0.3 g | 0.33 g |
| Flow rates | | |
| of liquid n-heptane | 0.02 cm3/min | 0.025 cm3/min |
| of gas n-heptane | 3.05 cm3/min | 3.82 cm3/min (CNTP) |
| Hydrogen flow rate | 120 cm3/min | 150 cm3/min (CNTP) |
| H2/heptane ratio | 39 | 39 |

Figure 7:
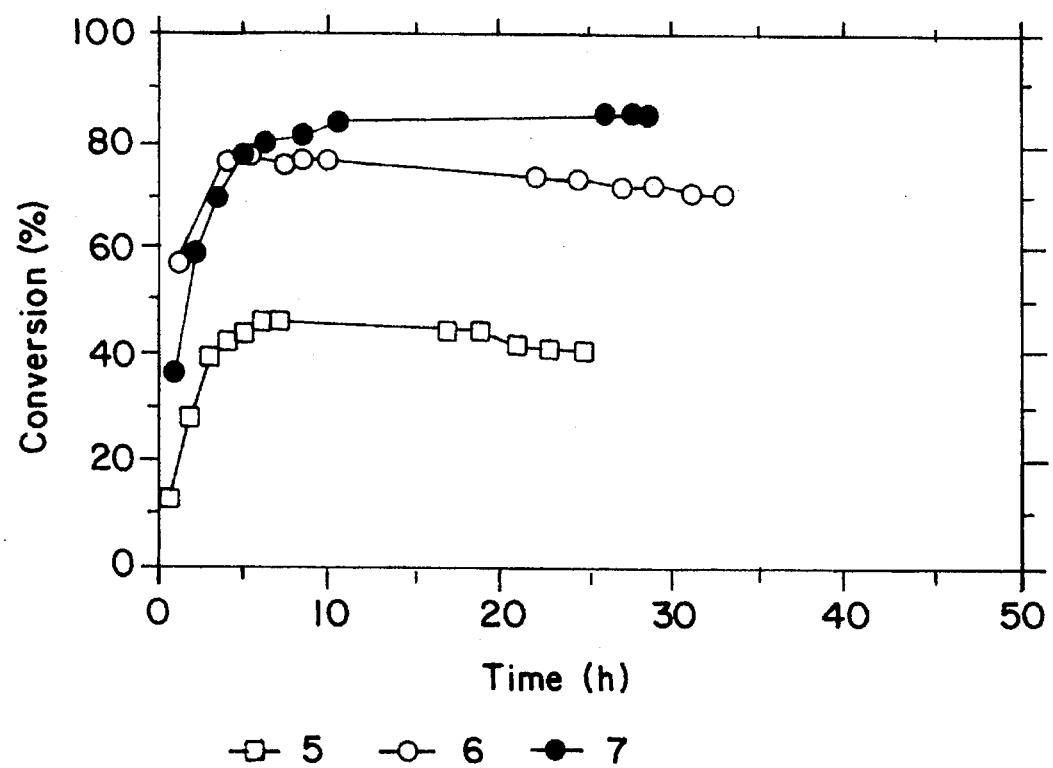
FIG. 7 shows the conversion rate as a function of time (percentage of heptane molecules having reacted, i.e. isomerized or cracked)
Figure 8:
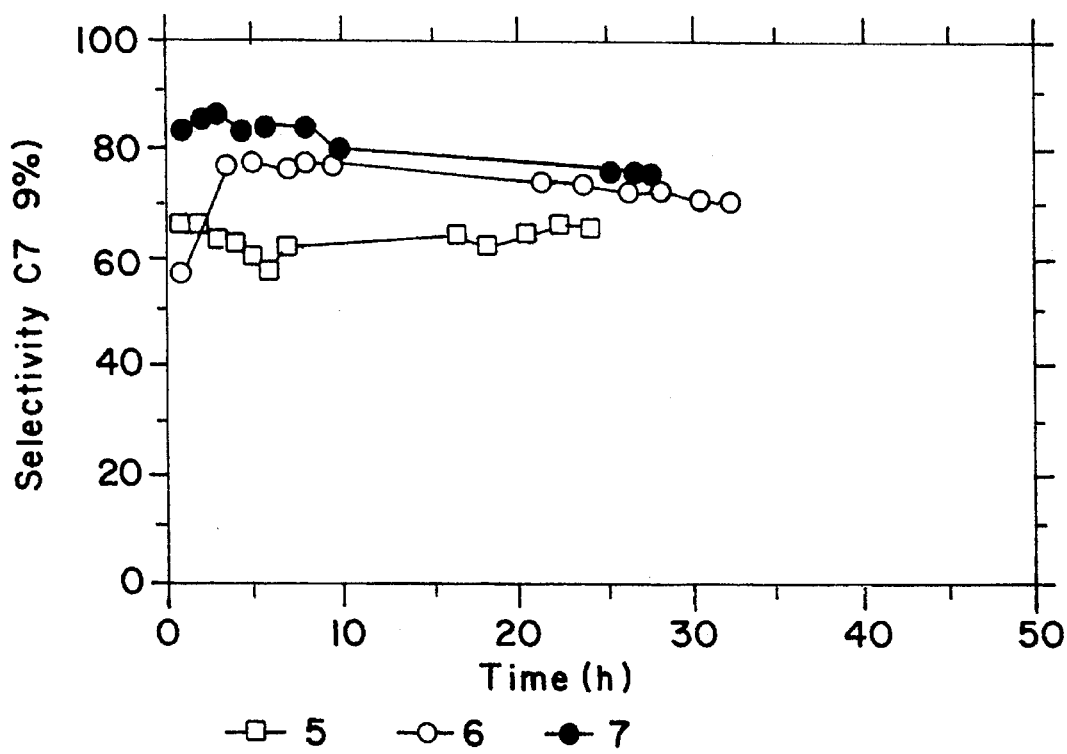
FIG. 8 shows the selectivity (percentage of molecules isomerized in relation to the molecules having reacted) for a catalyst according to the invention with various total pressure values.

The results obtained are shown in FIGS. 7 and 8. FIG. 7 shows, as a function of time, the conversion rate (percentage of heptane molecules which have reacted, that is to say which have isomerized or cracked), and FIG. 8 shows the selectivity (percentage of isomerized molecules in relation to molecules which have reacted).

It will be noted that the conversion rate becomes stationary for test 5 at about 41% after 20 hours, and for test 6 at about 70% after 25 hours, and for test 7 at about 85% after 20 hours.

The selectivity in the stationary state is 62% for test 5, 75% for test 6, and 78% for test 7.

A comparison with Example 1 is even more revealing here.

|  | Conversion Rate | Selectivity |
|---|---|---|
| Example 1 | 34% | 25% |
| Test 5 | 41% | 62% |
| Test 6 | 70% | 759 |
| Test 7 | 85% | 78% |

Example 4

Synthesis of results

Figure 9:
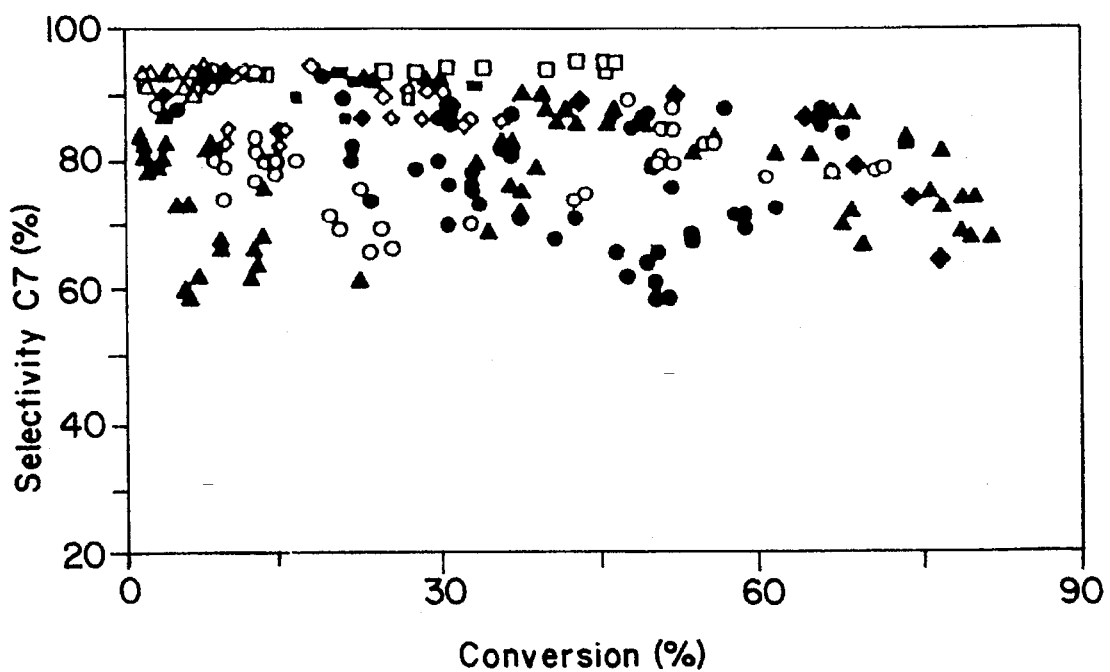
FIG. 9 shows the values for conversion rates and selectivities in a state of equilibrium, taken during a number of tests where the parameters of the isomerisation reaction: temperature, pressure, concentration of n-heptane in the mixture, flow rate, were varied for a catalyst according to the invention.

FIG. 9 gives the values of the conversion rates and selectivities in a state of equilibrium which are taken during various tests where the various parameters of the isomerisation reaction are varied: temperature, pressure, concentration of n-heptane in the mixture, flow rate. The conversion rates are plotted on the m-axis, and selectivities are plotted on the x-axis. Despite some scattering, it is noted that almost no point has a selectivity of less than 60%, and that points with a conversion rate of close to 75% have a selectivity close to 90%. Moreover, the main axis of the cloud of points is parallel to the x-axis which means that selectivity does not depend on conversion rate.

This drawing can advantageously be compared to FIG. 6 (example 2) which relates to the isomerisation of n-heptane in the presence of Pt-zeolite where the selectivity-conversion rate correlation is clearly negative and where the selectivity does not exceed about 40% for a rate of 75%.

Example 5

Figure 10:
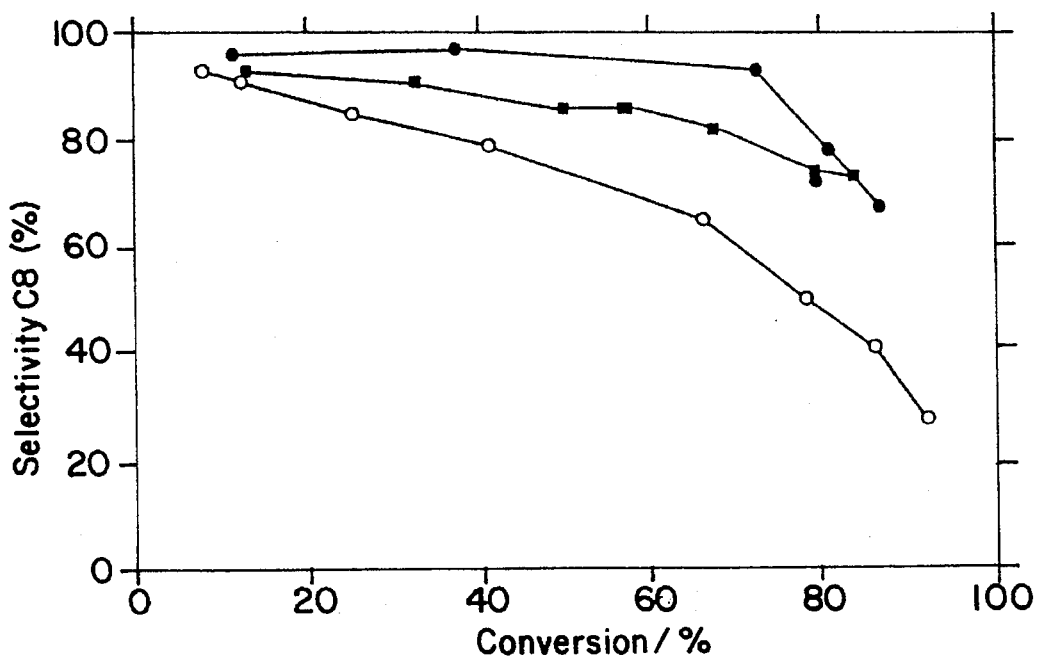
FIG. 10 gives the selectivity as a function of the conversion rate, during isomerisation of the n-octane carried out in the presence of catalysts with a molybdenum oxycarbide base according to the invention or in the presence of the Pt-zeolithic catalyst according to the prior art.

The selectivity curves as a function of the conversion rate are plotted for isomerisation of n-octane (FIG. 10). The catalysts used are prior art Pt-zeolite (as in Example 4), and molybdenum oxycarbide which is obtained in two ways: from $MoO_3$ so as to give an oxycarbide with a specific surface area of 140 $m^2/g$, as described hereinabove, or from $Mo_2C$ with a large specific surface area (125 $m^2/g$) which is itself obtained by reacting gaseous $MoO_3$ on a reactive carbon with a high specific surface area (as described in the application EP 0396475, seen above), the carbide then being treated in oxygen (in air, at 350° C. for 14 h).

The catalytic reactions were carried out under pressure. In FIG. 10, the names $MoO_3$ and $Mo_2C$ represent the corresponding oxycarbides.

It is seen there too that when conversion rates are very high the selectivity which is essentially acyclic (cyclic products do not actually exceed about 2%) varies little for the reaction in the presence of molybdenum oxycarbides, whilst this is not the case with the conventional catalyst.

This is of great importance industrially because it can be seen that the conversion yield is high, whereas with the Pt-zeolithic catalyst a conversion rate not in excess of 40% had to suffice.

Example 6

This example is concerned with the isomerisation of hydrocarbons in C10 and C20.

The isomerisation operation was carried out in the presence of oxycarbide obtained from $MoO_3$, as in the previous example, and with a pressure of 7 bars.

The results are given in Table 2 hereinafter showing the conversion rate and corresponding selectivity.

TABLE 2

|  | Conversion (%) | Selectivity (%) |
|---|---|---|
| C10 | 40 | 94 |
|  | 60 | 90 |
| C20 | 39 | 91 |
|  | 62 | 89 |

It can be seen that both a high conversion rate and a high selectivity are obtained; also, it could be noted that more than half the isomers obtained were multi-branched, that is to say that they had two or more substituted carbon atoms, which represents a certain advantage, with the presence of cyclic isomers still remaining very low.

These results are quite unusual for long chain hydrocarbons of this type.

Example 7

This example is concerned with the isomerisation of n-heptane in the presence of a catalyst with an oxycarbide base deposited on a SiC support with a large specific surface area of 127 $m^2/g$.

The support was obtained according to the process of French Patent 2621904, from grains of reactive carbon with a specific BET surface area of 987 $m^2/g$.

The support was impregnated with ammonium heptamolybdate which has been calcined at 550° C. for 2 hours and then treated directly with the reaction gas containing n-heptane at 350° C. at 20 bars, the ratio of volume of H2 to n-heptane being 40, in order to obtain the catalyst with a base of molybdenum oxycarbide with a large specific surface area.

The isomerisation treatment was continued under the same conditions. The ratio by weight of molybdenum oxycarbide to SiC support was 15%.

As in the previous examples, high values were obtained for the selectivity (92%) with a high conversion rate (83%) which also remained constant over time.

What is claimed is:

1. A process for the isomerization of straight chain hydrocarbons having at least seven carbon atoms, comprising forming a reaction mixture including at least one straight chain hydrocarbon having at least seven carbon atoms and hydrogen, and passing the reaction mixture over a catalyst comprising a molybdenum compound, said catalyst having at least a surface portion thereof formed of molybdenum carbide partially oxidized in the form of at least one oxycarbide.

2. A process according to claim 1, wherein the catalyst is prepared by reacting volatile $MoO_3$, on carbon with a large specific surface area to form molybdenum carbide and then activating the molybdenum carbide by oxidation in a current of oxidizing gas at a temperature of between 250° and 450° C.

3. A process according to claim 1, wherein the catalyst is prepared by carbonizing a paste comprising a mixture of an organic resin, and molybdenum powder or a reducible compound of molybdenum, heating the carbonized mixture to a temperature which is sufficient to reduce the molybdenum compound and to carburize the molybdenum obtained to form molybdenum carbide, and then activating the molybdenum carbide formed by oxidation in a current of oxidizing gas at a temperature of between 250° and 450° C.

4. A process according to claim 1, wherein the catalyst is obtained by immersing a mineral support into a suspension of Mo or of a reducible Mo compound in a carbonizable organic liquid, carbonizing the suspension impregnating the support, reducing the Mo compound to molybdenum, carburizing the molybdenum obtained to form molybdenum carbide, and finally activating the molybdenum carbide formed by oxidation in a current of oxidizing gas at a temperature of between 250° and 450° C.

5. A process according to one of claim 2, wherein the catalyst is subjected, prior to passage of the reaction mixture to be isomerized, to a treatment comprising passing a mixture, at atmospheric pressure, of n-hexane and hydrogen over the catalyst at a temperature of between 250° and 450° C.

6. A process according to claim 1, wherein the catalyst is obtained by superficial oxidation of metallic Mo into $MoO_3$ and partially carburizing the $MoO_3$ by passage of the reaction mixture which contains hydrogen and the at least one hydrocarbon at a temperature of between 250° and 450° C.

7. A process according to claim 1, wherein the catalyst is obtained from $MoO_3$ which is partly carburized by passage of the reaction mixture which contains hydrogen and the at least one hydrocarbon at a temperature of between 250° and 450° C.

8. A process according to claim 6 wherein before passing the reaction mixture over the molybdenum oxide $MoO_3$ the oxide is partly carburized by passage of a mixture of n-hexane and hydrogen at a temperature of between 250° and 450° C.

9. A process according to claim 1 wherein the catalyst is obtained from a porous support of a product which interacts with molybdenum oxide $MoO_3$, coated with a layer of molybdenum oxide $MoO_3$, which is then partly carburized by passage of a mixture of hydrocarbons and hydrogen at a temperature of between 250° and 450° C.

10. A process according to claim 9, wherein the support which slightly interacts with molybdenum oxide is selected from the group consisting of oxides $TiO_2$, $SiO_2$, and $ZrO_2$.

11. A process according to claim 9, wherein the support which slightly interacts with molybdenum oxide is of silicon carbide SiC.

12. A process according to claim 9 wherein the porous support is covered with a layer of $MoO_3$ by impregnation with an aqueous solution of ammonium heptamolybdate of a quantity such that the content measured of molybdenum metal is between 5 and 16% of the weight of the support, dried for 8 to 20 hours at a temperature of between 100° and 150° C., then calcined in air at a temperature of between 400° and 600° C. to transform the, heptamolybdate into $MoO_3$.

13. A process according to claim 9 wherein the mixture of hydrocarbons and hydrogen is the reaction mixture.

14. A process according to claim 9 wherein the mixture of hydrocarbons and hydrogen is initially a mixture of n-hexane and hydrogen and secondly the reaction mixture.

15. A process according to claim 1 wherein the at least one hydrocarbon is n-heptane.

16. A process according to claim 1 wherein the reaction mixture contains at least one hydrocarbon containing from 8 to 10 carbon atoms.

17. A process according to claim 1, wherein the mixture is passed over the catalyst at a temperature of 250° to 450° C., at a concentration of the at least one hydrocarbon in the mixture between 1 and 70%, and a total pressure for the mixture between 100 and 2000 kPa.

* * * * *